US00PP24309P3

(12) United States Plant Patent
Bors

(10) Patent No.: US PP24,309 P3
(45) Date of Patent: Mar. 11, 2014

(54) COLEUS PLANT NAMED 'JPN10'

(50) Latin Name: ***Solenostemon* sp.**
Varietal Denomination: Jpn10

(75) Inventor: Robert H. Bors, Saskatoon (CA)

(73) Assignee: University of Saskatchewan, Saskatoon, Saskatchewan (CA)

( * ) Notice: Subject to any disclaimer, the term of this patent is extended or adjusted under 35 U.S.C. 154(b) by 90 days.

(21) Appl. No.: 13/506,719

(22) Filed: May 10, 2012

(65) Prior Publication Data

US 2013/0305420 P1 Nov. 14, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Wendy C Haas

(74) *Attorney, Agent, or Firm* — Barbara Campbell; Cochran Freund & Young LLC

(57) ABSTRACT

A Coleus plant particularly distinguished by unique elongated, bronze and orange-colored secondary leaflets resembling a lobster claw and attached to the main leaf by single narrow veins, is disclosed.

2 Drawing Sheets

Genus and species: *Solenostemon* sp.
Variety denomination: 'Jpn10'.

BACKGROUND OF THE NEW PLANT

The present invention comprises a new and distinct variety of Coleus, botanically known as *Solenostemon* sp., and hereinafter referred to by the variety name 'Jpn10'. The new variety originated from an open pollination conducted in Saskatoon, Saskatchewan, Canada in January 2008. The female parent was the Coleus plant 'E208' (unpatented), and the male was an unknown Coleus plant (unpatented). The seeds produced by the open-pollination were sown in March 2008. A single plant selection was chosen for further evaluation and asexual propagation in December 2008.

The new plant was first asexually propagated in December 2008 in Saskatoon, Saskatchewan, Canada and has been asexually reproduced by vegetative cuttings for three years in Saskatoon, Saskatchewan, Canada. The present invention has been found to retain its distinctive characteristics through successive asexual propagations by vegetative cuttings.

'Jpn10' has not been made publicly available or sold more than one year prior to the filing date of this application.

SUMMARY OF THE NEW PLANT

The following are the most outstanding and distinguishing characteristics of the new variety when grown under normal horticultural practices in Saskatoon, Saskatchewan, Canada and Litchfield, Mich.

1. Unique elongated, bronze and orange-colored secondary leaflets resembling a lobster claw and attached to the main leaf by single narrow veins.

DESCRIPTION OF THE PHOTOGRAPHS

This new Coleus plant is illustrated by the accompanying photographs which show the overall plant habit, and foliage of the plant. The colors are as true as can be reasonably obtained by conventional photographic procedures. The photographs are of a 4.5 month-old plant grown in a greenhouse in Litchfield, Mich. The photographs were taken in November 2011.

DESCRIPTION OF THE NEW VARIETY

Figure 1:
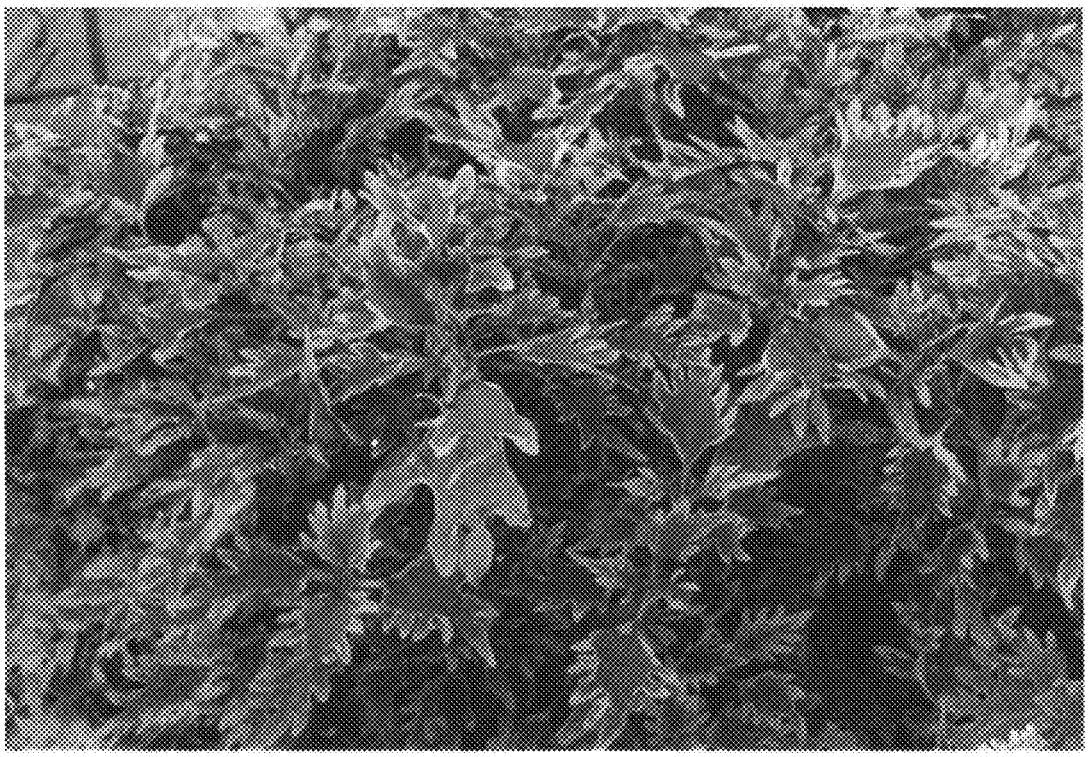
FIG. 1 shows the whole plant, including habit and foliage.
Figure 2:
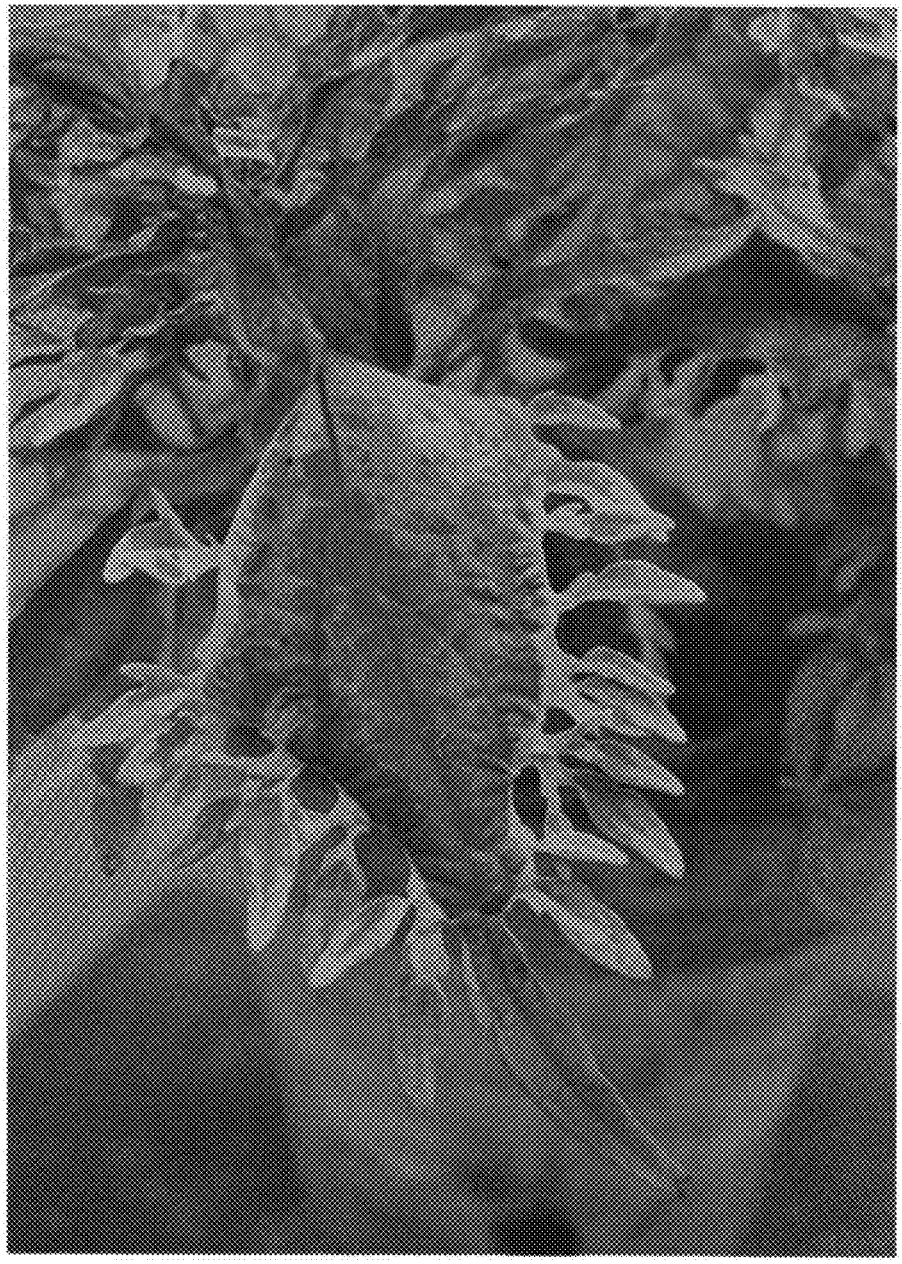
FIG. 2 shows a close-up of the foliage.

The following detailed descriptions set forth the distinctive characteristics of 'Jpn10'. The data which defines these characteristics were collected from asexual reproductions carried out in Saskatoon, Saskatchewan, Canada. The plant history was taken in October 2011 on 16-week old plants grown in a greenhouse in Litchfield, Mich. Color references were taken under natural light and are to The R.H.S. Colour Chart of The Royal Horticultural Society of London (R.H.S.), fifth edition (2007).

Classification:
- *Family*.—Lamiaceae.
- *Botanical name*.—*Solenostemon* sp.
- *Common name*.—Coleus.
- *Denomination*.—'Jpn10'.

Parentage: Open-pollination between the female coleus plant 'E208' (unpatented) and an unknown male coleus plant.

Plant:
- *Type*.—Annual.
- *Habit*.—Upright, basal-branched.
- *Height* (*measured from the top of the soil*).—43.2 cm.
- *Width* (*horizontal plant diameter*).—48.3 cm.
- *Time to produce a finished plant*.—About 6 to 8 weeks.
- *Time to initiate and develop roots*.—About 3 weeks.
- *Root description and habit*.—White roots, fibrous, and branching.
- *Propagation type*.—Vegetative cuttings.

Branches:
- *Quantity per plant*.—6 primary branches; 22 to 40 secondary branches.
- *Length*.—20.3 cm to 25.4 cm.
- *Internode length*.—1.9 cm to 2.5 cm.
- *Diameter* (*from midpoint*).—0.3 cm.

*Color*.—RHS 145D (Yellow-Green).
*Texture*.—Smooth.
*Pubescence*.—Absent.
*Petiole*.—Color: RHS 145D (Yellow-Green). Length: 1.3 cm to 3.8 cm. Diameter: 0.2 cm.

Leaves:
*Quantity of leaves per branch*.—About 12 to 22.
*Arrangement*.—Opposite to sub-opposite.
*Length*.—6.4 cm to 7.4 cm.
*Width*.—4.4 cm to 6.4 cm.
*Shape*.—Elliptic.
*Apex*.—Caudate.
*Base*.—Aequilateral.
*Margin*.—Parted.
*Color, immature*.—Upper surface: RHS 165C (Greyed-orange) and RHS 148B (Yellow-green) on the margins. Lower surface: RHS 184B (Greyed-purple).
*Color, mature*.—Upper surface: RHS 183A (Greyed-purple) and RHS 145A (Yellow-green). Lower surface: RHS 183A (Greyed-purple).
*Texture*.—Upper surface: Smooth. Lower surface: Smooth.
*Venation type*.—Venulate. Venation color: Upper surface: RHS 183A (Greyed-purple). Lower surface: RHS 145D (Yellow-green).

Secondary leaflets:
*Quantity per leaf*.—About 11 to 14.
*Length*.—0.6 cm to 1.9 cm.
*Width*.—0.1 cm to 0.5 cm.
*Shape*.—Lyrate.
*Apex*.—Rounded.
*Base*.—Rounded.
*Margin*.—Parted.
*Color*.—Upper surface: RHS 145A (Yellow-green). Lower surface: RHS 186D (Greyed-Purple).
*Texture*.—Upper surface: Smooth. Lower surface: Smooth.
*Venation type*.—Venulate.
*Venation color*.—Upper surface: RHS 183A (Greyed-purple). Lower surface: RHS 145D (Yellow-green).

Inflorescence: Single, bilabiate flowers arranged in verticallasters on terminal spikes; 5 petals.
*Fragrance*.—Absent.
*Spike*.—Length: 5.0 cm to 9.0 cm. Diameter: 2.0 cm to 2.5 cm. Quantity of verticillasters per spike: 9 flowers per node (9-12 nodes). Quantity of open flowers per verticillasters: Varies with age of plant.
*Flower bud*.—Length: 0.3 cm to 0.4 cm. Diameter: 0.1 cm to 0.15 cm. Color at tight bud: Light-green.
*Corolla*.—Diameter: 0.2 cm to 0.3 cm. Length: 0.7 cm to 0.8 cm. Petal arrangement: All 5 petals fused to form a tube. Banner width: 0.2 cm. Banner length: 0.2 cm. Keel length: 0.4 cm. Keel width: 0.2 cm.
*Calyx*.—Form: One single calyx tube formed by 5 fused sepals. Length: 0.2 cm. Diameter: 0.1 cm. Color (both inner and outer surfaces): Light green. Texture (both inner and outer surfaces): Pubescent.
*Pedicels*.—Length: 0.3 cm to 0.5 cm. Width (diameter): Less than 0.1 cm. Texture: Pubescent. Color: Light-green.

Reproductive organs:
*Stamens*.—Quantity per flower: 4. Filament color: White. Filament length: 0.3 cm to 0.4 cm.
*Pistils*.—Quantity per flower: 1. Length: 0.7 cm. Stigma color: Lavender. Stigma shape: Forked end. Style color: White.

Disease or insect resistance: No disease or insect resistance observed.

COMPARISON WITH PARENTAL AND COMMERCIAL VARIETY

'Jpn10' differs from the female Coleus parent 'E208' (unpatented) in that 'E208' has wide leaves with serrated edges and light-green colored leaves, while 'Jpn10' has deeply serrated and convoluted leaves and bronze and orange colored leaves. Additionally, 'E208' has larger leaves than 'Jpn10'.

'Jpn10' differs from the commercial comparison 'Inky Fingers' (patent status unknown) in that 'Jpn10' is a taller plant, has bronze-orange foliage, while 'Inky Fingers' is a shorter plant and has dark brown foliage. Additionally, the secondary leaflets of 'Jpn10' are often connected to the main leaf by single veins only 0.1 cm wide, while the secondary leaflets of 'Inky Fingers' are wholly attached to the main portion of the leaves by leaf sections about 0.4 cm to 0.6 cm wide.

I claim:

1. A new and distinct variety of Coleus plant as shown and described herein.

* * * * *